United States Patent [19]

Mori et al.

[11] Patent Number: 5,292,528
[45] Date of Patent: Mar. 8, 1994

[54] ORAL COMPOSITION

[75] Inventors: Shigeki Mori; Chiho Tomita, both of Takatsuki, Japan

[73] Assignee: Sunstar Kabushiki Kaisha, Osaka, Japan

[21] Appl. No.: 75,387

[22] Filed: Jun. 14, 1993

[51] Int. Cl.⁵ .......................... A61K 7/16; A61K 7/22; A61K 9/68; A61K 31/14
[52] U.S. Cl. ..................... 424/54; 424/401; 424/440; 424/48; 424/49; 514/642; 514/556
[58] Field of Search ................. 424/48–58, 424/401

[56] References Cited

U.S. PATENT DOCUMENTS

| | | | |
|---|---|---|---|
| 4,161,518 | 7/1979 | Wen et al. | 424/52 |
| 4,631,273 | 12/1986 | Blehm et al. | 514/29 |
| 4,842,766 | 6/1989 | Blehm et al. | 252/309 |
| 5,064,613 | 12/1991 | Higgs et al. | 422/16 |

*Primary Examiner*—Shep K. Rose
*Attorney, Agent, or Firm*—Wegner, Cantor, Mueller & Player

[57] ABSTRACT

There is disclosed an oral composition including an organosilicon-type quaternary ammonium salt immobilized on a water-insoluble solid carrier. In particularly, an oral composition in an aqueous system according to the present invention includes an organosilicon-type quaternary ammonium salt immobilized on a water-insoluble solid carrier in combination with at least one surfactant selected from the group consisting of polyoxyethylene-polyoxypropylene block copolymers and alkylolamides as a stabilizing agent; at least one thickening agent selected from the group consisting of nonionic thickening agents and cationic thickening agents; and optionally at least one alcohol selected from the group consisting of ethanol, propanol and isopropanol as a dispersing agent.

9 Claims, No Drawings

ORAL COMPOSITION

FIELD OF THE INVENTION

The present invention relates to a composition for oral cavities. More particularly, it relates to an oral composition having bactericidal activity to eliminate microorganisms in oral cavities, thereby exhibiting excellent plaque-controlling effect.

BACKGROUND OF THE INVENTION

It is well known that organosilicon-type quaternary ammonium salts immobilized on water-insoluble solid carriers (hereinafter referred to as organosilicon-type immobilized bactericides) have antibacterial activity. The bactericides of this type have been used as antibacterial agents for fiber treatment, as water treatment agents or as antibacterial agents to be incorporated into plastics (see, e.g., JP-A 177284/1987, JP-A 196810/1991 and JP-B 019860/1977). The application of organosilicon-type immobilized bactericides has not yet, however, been proposed in the field of oral hygiene.

In the field of oral hygiene, it is well known that conventional water-soluble quaternary ammonium compounds such as cetylpyridinium chloride or benzethonium chloride can be stably blended into dentifrice (see, e.g., JP-A 85310/1986 and U.S. Pat. No. 5,035,880). There is, however, no disclosure of water-insoluble immobilized bactericides in any literature of this field.

In general, organosilicon-type immobilized bactericides have a cationic character to react with any anionic ingredient, such as a foaming agent or a thickening agent, which is usually used in conventional oral compositions, thereby causing a significant decrease in their antibacterial activity. Further, organosilicon-type immobilized bactericides in particulate form have a tendency to aggregate in an aqueous system, so that these particles can hardly be dispersed, thereby making it difficult to attain uniform blending of these bactericides into an aqueous oral composition. Therefore, when an organosilicon-type immobilized bactericide is used in an aqueous system, it is necessary to devise some means for stabilization of this bactericide.

SUMMARY OF THE INVENTION

Under these circumstances, the present inventors have intensively studied to provide an oral composition comprising an organosilicon-type immobilized bactericide in a stable form. As the result, they have found that water-insoluble immobilized bactericides of the organosilicon type can be satisfactorily utilized for oral compositions. They have also found that the effects of organosilicon-type immobilized bactericides in an aqueous system can be remarkably improved by blending with a particular stabilizing agent and a particular thickening agent, and these effects can be further improved by addition of a particular alcohol, thereby completing the present invention.

Thus, the present invention provides an oral composition comprising an organosilicon-type quaternary ammonium salt immobilized on a water-insoluble solid carrier. In particular, an oral composition in an aqueous system according to the present invention comprises an organosilicon-type quaternary ammonium salt immobilized on a water-insoluble solid carrier in combination with at least one surfactant selected from the group consisting of polyoxyethylene-polyoxypropylene block copolymers and alkylolamides as a stabilizing agent; at least one thickening agent selected from the group consisting of nonionic thickening agents and cationic thickening agents; and optionally at least one alcohol selected from the group consisting of ethanol, propanol and isopropanol as a dispersing agent. The oral composition of the present invention can exhibit excellent plaque-controlling effect not only by attaining effective bactericidal action and elimination of microorganisms in oral cavities but also by preventing accumulation and calcification of their products.

DETAILED DESCRIPTION OF THE INVENTION

The oral composition of the present invention contains an organosilicon-type quaternary ammonium salt as a bactericide, which is immobilized on a water-insoluble solid carrier. The organosilicon-type quaternary ammonium salt used in the present invention is a well-known compound of the general formula:

$$R^1{}_3N^+R^2SiR^3{}_nX_{3-n}\cdot Y^-  \qquad (I)$$

wherein X is a hydrolyzable group such as halogen, alkoxy or acyl; Y is chlorine or bromine; $R^1$'s are independently monovalent aliphatic hydrocarbon groups having 1 to 22 carbon atoms, with particularly preferred being the case where two of three $R^1$'s are both methyl and the other $R^1$ is alkyl having 8 to 22 carbon atoms; $R^2$ is a divalent hydrocarbon group, with particularly preferred $R^2$ being alkylene having 2 to 4 carbon atoms or a group of the formula: —$CH_2CH_2CH_2NHCH_2CH_2$—; $R^3$ is lower alkyl such as methyl, phenyl or a group of the formula: $CF_3CH_2CH_2$—; n is an integer of 0 which is preferred, 1 or 2. This compound is usually available as an alcoholic solution from various commercial sources.

Preferred are the organosilicon-type quaternary ammonium salts of the general formula:

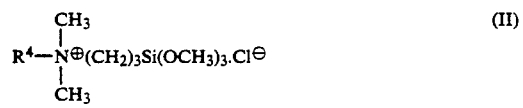

$$R^4-\overset{\overset{\displaystyle CH_3}{|}}{\underset{\underset{\displaystyle CH_3}{|}}{N^\oplus}}(CH_2)_3Si(OCH_3)_3\cdot Cl^\ominus \qquad (II)$$

wherein $R^4$ is alkyl having 8 to 22 carbon atoms.

The water-insoluble solid carrier for immobilization of an organosilicon-type quaternary ammonium salt may be made of either inorganic or organic material. It may also be made of either synthetic or natural substance. Examples of the solid carrier are metals, metal oxides, metal carbonates, metal phosphates and hydrogenphosphates, siliceous materials, cellulosic materials, resins and plastics. Particularly preferred are metals such as iron, aluminum, copper and nickel; metal oxides such as titanium oxide, alumina, zinc oxide, magnesium oxide, iron oxide; metal carbonates such as calcium carbonate and magnesium carbonate; metal hydrogenphosphates such as calcium hydrogen-phosphate; siliceous materials such as glass, silica, diatomaceous earth, quartz powder, mica, zeolite, aluminum silicate, aluminum calcium silicate, magnesium silicate and zirconium silicate; resins and plastics such as polyester, polyamide, cellulose acetate, rayon, polystyrene, polyethylene, polypropylene, epoxy resins, phenol resins, silicone resins and polycarbonate resins; cellulosic materials such as wood, cotton and linen; and other natural organic substances such as cellulose powder.

The organosilicon-type quaternary ammonium salt can be immobilized on a water-insoluble solid carrier as described above by any conventional method to obtain an organosilicon-type immobilized bactericide. For example, a solution of the organosilicon-type quaternary ammonium salt is applied to the water-insoluble solid carrier by immersion or spraying, followed by drying or heating, thereby attaining the desired immobilization. Preferably, the water-insoluble solid carrier is coated with an aqueous or organic solvent solution of the organosilicon-type quaternary ammonium salt. Such a treatment solution can readily be prepared by adding the corresponding hydrolyzable silane to water or an organic solvent such as methanol, ethanol or hexane. The concentration of the organosilicon-type quaternary ammonium salt in the treatment solution is preferably in the range of 0.1% to 10% by weight, because satisfactory results can be obtained. When the coated surface of the water-insoluble solid carrier is air-dried or heated, the coating of the organosilicon-type quaternary ammonium salt is immobilized on the surface of the solid carrier. If the solid carrier thus treated is heated at a temperature of 65° C. to 100° C. for several minutes, the coating of the organosilicon-type quaternary ammonium salt is more tightly immobilized on the surface of the solid carrier. When desired, a conventional silanol condensation catalyst such as water can be added to the treatment solution for the purpose of enhancing the silanol condensation properties to form improved bondings of the related compounds.

The oral composition of the present invention may contain an organosilicon-type immobilized bactericide at an amount of 0.001% to 50% by weight, preferably 0.1% to 20% by weight, based on the total weight of the composition. When the amount thereof is less than 0.001% by weight, sufficient microorganism elimination effects cannot be attained. When the amount thereof is greater than 50% by weight, the characteristics of the composition will become unstable.

The oral composition in an aqueous system (i.e., aqueous oral composition) according to the present invention may preferably contain at least one surfactant selected from the group consisting of polyoxyethylene-polyoxypropylene block copolymers and alkylolamides.

The polyoxyethylene-polyoxypropylene block copolymers are conventional nonionic surfactants which are commercially available, for example, under the trade name "PLURONIC" from BASF Corporation in U.S.A.

The surfactants of this type are chemically defined by the percent by weight (wt %) of polyoxypropylene hydrophobic moieties and the percent by weight (wt %) of polyoxyethylene hydrophilic moieties, based on the total molecular weight. Preferred are those which the molecular weight of the hydrophobic groups (polyoxypropylene) is 1400 to 4000 and the ratio of the hydrophilic groups (polyoxyethylene) in the total molecular weight is in the range of 30% to 80% by weight.

In the aqueous oral composition of the present invention, the polyoxyethylene-polyoxypropylene block copolymer not only acts as an excellent surfactant but also significantly improves the microorganism elimination effects of the organosilicon-type immobilized bactericide.

The polyoxyethylene-polyoxypropylene block copolymer may be blended at an amount of 0.01% to 14% by weight, preferably 0.1% to 10% by weight, based on the total weight of the composition. When the amount thereof is less than 0.01% by weight, sufficient surface-active effects cannot be attained. When the amount thereof is greater than 14% by weight, gelation will occur and viscosity will become too high under the coexistence of a thickening agent, thereby making it impossible to obtain satisfactory characteristics as an oral composition.

The alkylolamides used in the present invention are conventional nonionic surfactants of the general formula:

or

wherein $R^5$ is alkyl having 8 to 24 carbon atoms. Examples of the alkylolamide are lauric acid monoethanolamide, lauric acid diethanolamide, coconut oil fatty acid monoethanolamide and coconut oil fatty acid diethanolamide. The alkylolamide is commercially available, for example, under the trade name "TOHOL" from Toho Kagaku Kogyo, Co., Ltd.

In the aqueous oral composition of the present invention, the alkylolamide not only acts as an excellent surfactant but also significantly improves the microorganism elimination effects of the organosilicon-type immobilized bactericide.

The alkylolamide may be blended at an amount of 0.001% to 50% by weight, preferably 0.1% to 10% by weight, based on the total weight of the composition. When the amount thereof is less than 0.001% by weight, sufficient surface-active effects cannot be attained. When the amount thereof is greater than 50% by weight, the deterioration of stability will be caused, such as liquid separation.

The aqueous oral composition of the present invention may preferably contain at least one thickening agent selected from the group consisting of nonionic or cationic thickening agents, which will not reduce the microorganism elimination effects of the organosilicon-type immobilized bactericide.

Examples of the nonionic thickening agent are hydroxyethyl cellulose, methyl cellulose, hydroxymethyl cellulose, hydroxypropylmethyl cellulose and water-soluble cellulose ethers (e.g., those derived from hydroxyethyl cellulose, hydroxypropylmethyl cellulose, methyl cellulose or hydroxypropyl cellulose) which are hydrophobically modified with hydrocarbon groups having 8 to 24 carbon atoms. Examples of the cationic thickening agent are cationically-modified hydroxyethyl cellulose such as hydroxyethyl cellulose with 3-chloro-2-hydroxypropyltrimethylammonium chloride added thereto, and cationically-modified guar gum. These thickening agents can be used alone or in combination. The amount of thickening agent to be used is usually in the range of 0.01% to 20% by weight, based on the total weight of the composition.

The aqueous oral composition of the present invention may preferably contain at least one alcohol selected from the group consisting of ethanol, propanol and isopropanol. When such an alcohol is blended in the composition, the alcohol not only acts as a dispersing agent for preventing the aggregation of the organosilicon-type immobilized bactericide particles but also significantly improves the microorganism elimination effects of the organosilicon-type immobilized bactericide.

The amount of alcohol to be used is usually in the range of 0.01% to 60% by weight, preferably 0.1% to 30% by weight, based on the total weight of the composition. When the amount is less than 0.01% by weight, sufficient dispersing effects cannot be attained. When the amount is greater than 60% by weight, the deterioration of property stability will be caused, such as liquid separation.

The oral composition of the present invention may be formulated into a conventional preparation such as toothpowder, toothpaste, toothwash, dental ointment, mouth washes, gargles, chewing gum and cream by any conventional method. Depending upon its desired application such as dentifrice and preparation for gingival massage, nonionic and anionic surfactants, polishing agents, flavoring agents, thickening agents, viscosity builders, sweeteners and other therapeutic agents can also be blended into the composition, so long as the effects of the present invention will not be deteriorated.

In case of dentifrice, calcium secondary phosphate dihydrate and anhydrate, calcium primary phosphate, calcium tertiary phosphate, calcium carbonate, calcium pyrophosphate, aluminum hydroxide, alumina, silicic acid anhydride, silica gel, aluminum silicate, insoluble sodium metaphosphate, magnesium tertiary phosphate, magnesium carbonate, calcium sulfate, polymethyl methacrylate, bentonite, zirconium silicate and synthetic resins can be blended into the composition alone or in combination. The amount of ingredient to be used is usually in the range of 5.0% to 90% by weight, based on the total weight of the composition. Particularly, in case of toothpaste, the amount thereof is in the range of 5% to 60% by weight, based on the total weight of the composition.

Examples of the nonionic surfactant are sucrose fatty acid esters, polyoxyethylene sorbitan fatty acid esters such as polyoxyethylene sorbitan monolaurate and polyoxyethylene sorbitan monostearate, polyoxyethylene hardened castor oil, polyoxyethylene fatty acid esters, fatty acid monoglycerides, polyoxyethylene higher alcohol ethers and polyoxyethylene polyoxypropylene fatty acid esters.

Examples of the anionic surfactant are water-soluble salts of higher alkyl sulfate esters with the alkyl having 8 to 18 carbon atoms, such as sodium lauryl sulfate and sodium myristyl sulfate, α-olefin sulfonate, higher fatty acid sodium monoglyceride monosulfate, sodium N-methyl-N-palmitoyl tauride, sodium N-lauroyl-β-alanine, lauroyl sarcosinate and sodium N-long chain acyl basic amino acids.

These surfactants can be used alone or in combination. The amount of surfactant to be used is usually in the range of 0.01% to 20% by weight, preferably 0.05% to 10% by weight, based on the total weight of the composition.

Examples of the thickening agent are cellulose derivatives such as sodium carboxymethyl cellulose; alginates of alkali metals, such as sodium alginate; propylene glycol alginate esters; gums such as xanthan gum, tragacanth gum, karaya gum, arabic gum and carrageenan; synthetic thickening agents such as polyvinyl alcohol, sodium polyacrylate, carboxyvinyl polymers and polyvinyl pyrrolidone; and inorganic thickening agents such as silica gel, aluminum silica gel, bee gum and Laponite. These thickening agents can be used alone or in combination. The amount of thickening agent to be used is usually in the range of 0.3% to 5% by weight, based on the total weight of the composition.

Examples of the viscosity builder are sorbit, glycerin, ethylene glycol, propylene glycol, 1,3-butylene glycol, polyethylene glycol, polypropylene glycol, xylitol, maltitol and lactitol. These viscosity builders may be used alone or in combination. The amount of viscosity builder to be used is usually in the range of 5% to 70% by weight, based on the total weight of the composition.

Examples of the flavoring agent are menthol carboxylic acid, anethole, eugenol, methyl salicylate, limonene, cymene, n-decyl alcohol, citronellol, α-terpineol, methyl acetate, citronellyl acetate, methyl eugenol, cineole, linalool, ethyl linalool, vanillin, thymol, spearmint oil, peppermint oil, lemon oil, orange oil, sage oil, rosemary oil, cinnamon oil, pellira oil, gaultheria oil, clove oil and eucalyptus oil. These flavoring agents may be used alone or in combination. The amount of flavoring agent to be used is usually in the range of about 0.1% to 10% by weight, preferably about 0.5% to 5% by weight, based on the total weight of the composition.

Examples of the sweetener are saccharin sodium, Acesulfame K, stevioside, neo-hesperidyl dihydrochalcone, glycyrrhizin, perillartine, thaumatin, aspartylphenylalanine methyl ester and p-methoxycinnamic aldehyde. These sweeteners may be used alone or in combination. The amount of sweetener to be used is usually in the range of 0.01% to 1% by weight, preferably 0.05% to 0.5% by weight, based on the total weight of the composition.

Examples of the therapeutic agent are cationic bactericides such as cetylpyridium chloride and chlorhexidine salts; nonionic bactericides such as tricrosan; amphoteric bactericides such as dodecyldiaminoethylglycine; enzymes such as dextranase, amylase, protease, mutanase, lysozyme and lytic enzymes; monofluorophosphates of alkali metals, such as sodium monofluorophosphate and potassium monofluorophosphate; fluorides such as sodium fluoride and stannous fluoride; tranexamic acid and ε-aminocapric acid; aluminum chlorhydroxyl allantoin; dihydrocholesterol, glycyrrhizin salts, glycyrrhetic acid, glycerophosphate, chlorophyll, sodium chloride, caropeptide and water-soluble compounds of inorganic phosphoric acid. These therapeutic agents may be used alone or in combination.

The present invention will be further illustrated by way of the following experiments, examples and comparative examples, which are not to be construed to limit the scope thereof. Unless otherwise indicated, percents (%) are all by weight.

Experiments

Various organosilicon-type immobilized bactericides were prepared by immobilizing organisilicon-type quaternary ammonium salts of the general formula (II) on water-insoluble solid carriers as shown in Table 1, and these bactericides were evaluated for their bactericidal activities and microorganism elimination effects according to the following procedures. The results are shown in Table 1.

Procedures for evaluation of microorganism elimination effects (1) Preparation of test bacterial suspension The cultures of Streptococcus sobrinus OMZ176 were incubated in a brain-heart-infusion liquid medium under anaerobic conditions at 37° C. for 20 hours, and then harvested by centrifugation at 7000 rpm for 10 minutes. The bacterial cells thus obtained were washed with sterilized physiological saline and suspended in sterilized physiological saline to yield a bacterial concentration of about $10^7$ cells/ml ($OD_{560}=0.02$), resulting in a test bacterial suspension.

(2) Evaluation of microorganism elimination ratio (shake flask method)

A prescribed amount of the sample was put in a 100-ml Erlenmeyer flask, to which 36 ml of sterilized water was then added to achieve sufficient dispersion of the sample. The Erlenmeyer flask was placed in a thermostat at 37° C., to which 4 ml of the test bacterial suspension prepared in (1) was added, and the resulting mixture was shaken at 120 strokes/min. for 3 minutes.

The Erlenmeyer flask was removed from the thermostat and allowed to stand for some time, after which 1 ml of the supernatant was taken and diluted with sterilized physiological saline. Then, 0.1 ml of this dilution was smeared on a brain-heart-infusion agar plate, and this plate was incubated under anaerobic conditions at 37° C. for 48 hours, followed by counting of the colony number. The viable cell number after contact with the sample for 3 minutes can be calculated from the colony number.

The microorganism elimination ratio (%) of the sample was evaluated by the following equation, and it was determined that the sample had excellent microorganism elimination effects when exhibited a microorganism elimination ratio of 90% or more.

Microorganism elimination ratio (%) =

$$\frac{\left(\begin{array}{c}\text{Initial viable}\\\text{cell number}\end{array}\right) - \left(\begin{array}{c}\text{Viable cell number after}\\\text{contact after 3 minutes}\end{array}\right)}{(\text{Initial viable cell number})} \times 100$$

TABLE 1

| Sample No. | Solid carrier | $C_n$*) | Concentration (%) | Microorganism elimination ratio (%) |
|---|---|---|---|---|
| 1 | Cellulose powder | $C_{18}$ | 1.0 | 97 |
| 2 | Silica | $C_{18}$ | 1.0 | 96 |
| 3 | Calcium hydrogen-phosphate | $C_{18}$ | 1.0 | 97 |
| 4 | Zeolite | $C_{18}$ | 1.0 | 98 |
| 5 | Zeolite | $C_{18}$ | 0.0005 | 70 |
| 6 | Zeolite | $C_{18}$ | 50 | 99 |
| 7 | Zeolite | $C_6$ | 1.0 | 35 |
| 8 | Cellulose powder | — | 1.0 | 3 |
| 9 | Silica | — | 1.0 | 6 |
| 10 | Calcium hydrogen-carbonate | — | 1.0 | 5 |
| 11 | Zeolite | — | 1.0 | 8 |
| 12 | Control (water) | — | — | 0 |

*) The symbol "$C_n$" denotes the length of alkyl chain ($R^4$) in the organosilicon-type quaternary ammonium salts of the general formula (II); and the symbol "—" indicates no use of these quaternary ammonium salts immobilized on the solid carriers.

As can be seen from Table 1, the samples 1–7, particularly the samples 1–4 and 6, exhibited apparently higher microorganism elimination ratio, as compared with the samples 8–11 containing only the solid carrier on which the organosilicon-type quaternary ammonium salt was not immobilized. It was also found that the microorganism elimination effects of the samples 4–6 depend on the concentration of immobilized bactericides and the extremely high elimination ratio was obtained at a concentration of 0.001% to 50%. Further, stronger microorganism elimination effects were achieved in the case of longer alkyl chain length ($C_{18}$) than the case of shorter alkyl chain length ($C_6$) for the organosilicon-type quaternary ammonium salts.

Then, it was examined whether the addition of a particular alcohol as the dispersing agent had an influence on the microorganism elimination effects.

The sample 2 (shown in Table 1) as an organosilicon-type immobilized bactericide was mixed with any one of the alcohols (10 wt %) as shown in Table 2 below. The dispersing state of the resulting mixture was determined by visual observation and the microorganism elimination ratio was evaluated according to the procedures as described above. The results are shown in Table 2.

TABLE 2

| Dispersing agent | Dispersing state (by visual obs.) | Elimination ratio (%) |
|---|---|---|
| Ethanol | good | 99 |
| Isopropanol | good | 99 |
| 1,3-butylene glycol | good | 80 |
| Propylene glycol | good | 80 |
| Glycerin | good | 80 |
| No addition | poor | 80 |

As can be seen from Table 2, the mixtures prepared with the addition of ethanol or isopropanol exhibited extremely higher microorganism elimination effects as compared with those prepared with the addition of any other alcohol or no addition.

Next, it was examined whether the concentration of alcohol to be added had an influence on the improvement of the microorganism elimination effects.

The sample 2 (shown in Table 1) as an organosilicon-type immobilized bactericide was mixed with either ethanol or isopropanol at any one of the amounts as shown in Table 3 below. The microorganism elimination ratio was evaluated according to the procedures as described above. The results are shown in Table 3.

TABLE 3

| Dispersing agent | Amount (wt %) | Elimination ratio (%) |
|---|---|---|
| No addition | — | 80 |
| Ethanol | 0.01 | 94 |
|  | 1 | 99 |
|  | 10 | 99 |
|  | 30 | 99 |
| Isopropanol | 0.01 | 93 |
|  | 1 | 98 |
|  | 10 | 99 |
|  | 30 | 99 |

As can be seen from Table 3, the mixtures prepared with the addition of ethanol or isopropanol at an amount of 0.01 wt % or more exhibited an improvement of the microorganism elimination effects as compared with that prepared with no addition of alcohols.

EXAMPLE 1

An organosilicon-type quaternary ammonium salt of the general formula (II) wherein the alkyl chain $R^4$ has 18 carbon atoms was immobilized on the surface of silica powder particles to form an organosilicon-type immobilized bactericide. The organosilicon-type immobilized bactericide (1.0 wt %) was blended with PLURONIC F-88 (average polymerization degree: ethylene oxide, 194; and propylene oxide, 39; 2.0 wt %) as the stabilizing agent, hydroxyethyl cellulose (2.0 wt %) as the thickening agent, calcium hydrogenphosphate (30 wt %), glycerin (20 wt %), flavor (1 wt %), saccharin sodium (0.2 wt %) and water (the balance). The mixture was well stirred to give a dentifrice composition according to the conventional procedures. The resulting dentifrice composition was evaluated for microorganism elimination effects according to the procedures as described above. The microorganism elimination ratio of this composition was 92%.

The dentifrice composition of this example exhibited extremely strong microorganism elimination effects and stable characteristics with no occurrence of solid-liquid separation, because a polyoxyethylene-polyoxypropylene block copolymer and a nonionic thickening agent were used.

EXAMPLE 2

A dentifrice composition was prepared in the same manner as described in Example 1, except that cationically-modified hydroxyethyl cellulose (2.0 wt %) was used in place of hydroxyethyl cellulose as the thickening agent. The resulting dentifrice composition was evaluated for microorganism elimination effects according to the procedures as described above. The microorganism elimination ratio of this composition was 90%.

The dentifrice composition of this example exhibited extremely strong microorganism elimination effects and stable characteristics with no occurrence of solid-liquid separation, because a polyoxyethylene-polyoxypropylene block copolymer and a cationic thickening agent were used.

EXAMPLE 3

A dentifrice composition was prepared in the same manner as described in Example 1, except that PLURONIC F-127 (average polymerization degree: ethylene oxide, 196; and propylene oxide, 67; 2.0 wt %) was used in place of PLURONIC F-88 (average polymerization degree: ethylene oxide, 194; and propylene oxide, 39) as the stabilizing agent. The resulting dentifrice composition was evaluated for microorganism elimination effects according to the procedures as described above. The microorganism elimination ratio of this composition was 90%.

The dentifrice composition of this example exhibited extremely strong microorganism elimination effects and stable characteristics with no occurrence of solid-liquid separation, because a polyoxyethylene-polyoxypropylene block copolymer and a nonionic thickening agent were used.

EXAMPLE 4

A dentifrice composition was prepared in the same manner as described in Example 1, except that lauric acid diethanolamide (2.0 wt %) was used in place of PLURONIC F-88 as the stabilizing agent. The resulting dentifrice composition was evaluated for microorganism elimination effects according to the procedures as described above. The microorganism elimination ratio of this composition was 92%.

The dentifrice composition of this example exhibited extremely strong microorganism elimination effects and stable characteristics with no occurrence of solid-liquid separation, because an alkylolamide and a nonionic thickening agent were used.

EXAMPLE 5

A dentifrice composition was prepared in the same manner as described in Example 1, except that coconut oil fatty acid diethanolamide (2.0 wt %) was used in place of PLURONIC F-88 as the stabilizing agent. The resulting dentifrice composition was evaluated for microorganism elimination effects according to the procedures as described above. The microorganism elimination ratio of this composition was 90%.

The dentifrice composition of this example exhibited extremely strong microorganism elimination effects and stable characteristics with no occurrence of solid-liquid separation, because an alkylolamide and a nonionic thickening agent were used.

COMPARATIVE EXAMPLE 1

A dentifrice composition was prepared in the same manner as described in Example 1, except that polyoxyethylene sorbitan monolaurate (2.0 wt %) was used in place of PLURONIC F-88 as the stabilizing agent. The resulting dentifrice composition was evaluated for microorganism elimination effects according to the procedures as described above. The microorganism elimination ratio of this composition was 34%.

The dentifrice composition of this example did not exhibit satisfactory microorganism elimination effects, because a nonionic surfactant other than polyoxyethylene-polyoxypropylene block copolymers and alkylolamides was used as the stabilizing agent, although a nonionic hydroxypropyl methyl cellulose was used as the thickening agent, whereby the organosilicon-type immobilized bactericide was not stabilized.

COMPARATIVE EXAMPLE 2

A dentifrice composition was prepared in the same manner as described in Example 1, except that polyoxyethylene hardened castor oil (60 E.O.; 2.0 wt %) was used in place of PLURONIC F-88 as the stabilizing agent. The resulting dentifrice composition was evaluated for microorganism elimination effects according to the procedures as described above. The microorganism elimination ratio of this composition was 33%.

The dentifrice composition of this example did not exhibit satisfactory microorganism elimination effects, because a nonionic surfactant other than polyoxyethylene-polyoxypropylene block copolymers and alkylolamides was used as the stabilizing agent, although a nonionic hydroxypropyl methyl cellulose was used as the thickening agent, whereby the organosilicon-type immobilized bactericide was not stabilized.

COMPARATIVE EXAMPLE 3

A dentifrice composition was prepared in the same manner as described in Example 1, except that the organosilicon-type immobilized bactericide was not used. The resulting dentifrice composition was evaluated for microorganism elimination effects according to the procedures as described above. The microorganism elimination ratio of this composition was 5%.

The dentifrice composition of this comparative example did not exhibit microorganism elimination effects, because the organosilicon-type immobilized bactericide was not blended therein, although the same stabilizing agent and the same thickening agent as those used in Example 1 were used.

EXAMPLE 6

A dentifrice composition was prepared from the following formulation according to the conventional procedures.

| Ingredients | Amounts (wt %) |
| --- | --- |
| Sample 4 (shown in Table 1) | 0.5 |
| Cetylpyridium chloride | 0.1 |
| Sodium monofluorophosphate | 0.7 |
| PLURONIC F-88 | 2.0 |
| (average polymerization degree: ethylene oxide, 194; and propylene oxide, 39) | |
| Cationically-modified hydroxyethyl cellulose | 2.0 |
| Aluminum hydroxide | 20.0 |
| Glycerin | 20.0 |
| Flavor | 1.0 |
| Saccharin sodium | 0.2 |
| Purified water | Balance |

The dentifrice composition obtained was evaluated for the microorganism elimination ratio according to the procedures as described above, and it exhibited good microorganism elimination effects and excellent feeling of use.

EXAMPLE 7

A cream composition for gingival massage was prepared from the following formulation according to the conventional procedures.

| Ingredients | Amounts (wt %) |
| --- | --- |
| Sample 1 (shown in Table 1) | 5.0 |
| Tocopherol nicotinate | 0.5 |
| PLURONIC F-77 | 2.0 |
| (average polymerization degree: ethylene oxide, 104; and propylene oxide, 35) | |
| Hydrophobically-modified hydroxyethyl cellulose | 3.0 |
| [carbon number of hydrophobic groups, 18] | |
| Glycerin | 20.0 |
| Ethanol | 3.0 |
| Flavor | 0.6 |
| Dipotassium glycyrrhizinate | 0.1 |
| Purified water | Balance |

The cream composition for gingival massage obtained was evaluated for the microorganism elimination ratio according to the procedures as described above, and it exhibited good microorganism elimination effects and excellent feeling of use.

EXAMPLE 8

A toothpowder composition was prepared was prepared from the following formulation according to the conventional procedures.

| Ingredients | Amounts (wt %) |
| --- | --- |
| Sample 4 (shown in Table 1) | 2.0 |
| Calcium hydrogenphosphate | 50.0 |
| Calcium carbonate | 20.0 |
| Lauric acid diethanolamide | 1.0 |
| Glycerin | 20.0 |
| Flavor | 1.0 |
| Saccharin sodium | 0.1 |
| Purified water | Balance |

The toothpowder composition obtained was evaluated for the microorganism elimination ratio according to the procedures as described above, and it exhibited good microorganism elimination effects and excellent feeling of use.

EXAMPLE 9

A toothwash composition was prepared from the following formulation according to the conventional procedures.

| Ingredients | Amounts (wt %) |
| --- | --- |
| Sample 2 (shown in Table 1) | 0.5 |
| Cationically-modified cellulose | 2.0 |
| Coconut oil fatty acid diethanolamide | 1.0 |
| Sorbit | 30.0 |
| Saccharin sodium | 0.1 |
| Flavor | 1.0 |
| Chlorhexizine gluconate | 0.5 |
| Ethanol | 10.0 |
| Isopropanol | 5.0 |
| Methyl paraoxybenzoate | 0.1 |
| Water | Balance |

The toothwash composition obtained was evaluated for the microorganism elimination ratio according to the procedures as described above, and it exhibited good microorganism elimination effects and excellent feeling of use.

EXAMPLE 10

A mouth wash composition was prepared from the following formulation according to the conventional procedures.

| Ingredients | Amounts (wt %) |
| --- | --- |
| Sample 1 (shown in Table 1) | 0.5 |
| Glycerin | 10.0 |
| Ethanol | 15.0 |
| Saccharin sodium | 0.1 |
| Flavor | 0.3 |
| PLURONIC F-127 | 1.0 |
| (average polymerization degree: ethylene oxide, 196; and propylene oxide, 67) | |
| Cationically-modified guar gum | 0.2 |
| Paraoxybenzoate ester | 0.1 |
| Water | Balance |

The mouth wash composition obtained was evaluated for the microorganism elimination ratio according to the procedures as described above, and it exhibited good microorganism elimination effects and excellent feeling of use.

EXAMPLE 11

A chewing gum composition was prepared from the following formulation according to the conventional procedures.

| Ingredients | Amounts (g) |
|---|---|
| Gum base*) | 20 |
| Sugar | 58 |
| Glucose | 10 |
| Corn syrup | 10 |
| Hydroxyethyl cellulose | 1 |
| Flavor | 1 |
| | 100 g |
| *)Gum base was prepared from the following formulation. | |
| Sample 2 (as shown in Table 1) | 20 |
| Natural tickle | 15 |
| Vinyl acetate resin | 25 |
| Ester gum | 10 |
| Wax | 15 |
| Lauric acid diethanolamide | 5 |
| Isopropanol | 10 |
| | 100 g |

The chewing gum composition obtained was evaluated for the microorganism elimination ratio according to the procedures as described above, and it exhibited good microorganism elimination effects and excellent feeling of use.

EXAMPLE 12

A dental floss composition was prepared by immobilizing an organosilicon quaternary ammonium salt of the general formula (II) wherein the alkyl chain $R^4$ has 18 carbon atoms on the surface of nylon floss as the water-insoluble solid carrier.

The dental floss composition obtained was evaluated for the microorganism elimination ratio according to the procedures as described above, and it exhibited good microorganism elimination effects.

What is claimed is:

1. An oral hygiene composition selected from the group consisting of tooth powder, toothpaste, dermatologic ointment, mouth wash, gargle, chewing gum, dental cream, and dental floss, said composition comprising an organosilicon-type quaternary ammonium salt bactericide which has a tendency to aggregate in an aqueous system immobilized on a water-insoluble solid stabilizing carrier.

2. An oral hygiene composition according to claim 1, wherein the organosilicon-type quaternary ammonium salt is trialkoxysilylalkyltrialkylammonium halide.

3. An oral hygiene composition according to claim 1, wherein the water-insoluble solid carrier is selected from the group consisting of siliceous materials and cellulosic materials.

4. An oral hygiene composition according to claim 1, further comprising at least one surfactant selected from the group consisting of polyoxyethylene-polyoxypropylene block copolymers and alkylolamides.

5. An oral hygiene composition according to claim 1, further comprising at least one thickening agent selected from the group consisting of nonionic thickening agents and cationic thickening agents.

6. An oral hygiene composition according to claim 5, wherein the nonionic thickening agent is hydroxyethyl cellulose, hydroxypropylmethyl cellulose, hydrophobically-modified hydroxyethyl cellulose and hydrophobically-modified hydroxypropylmethyl cellulose.

7. An oral hygiene composition according to claim 5, wherein the cationic thickening agent is cationically-modified hydroxyethyl cellulose.

8. An oral hygiene composition according to claim 1, further comprising at least one alcohol selected from the group consisting of ethanol, propanol and isopropanol.

9. An oral hygiene composition according to claim 1, wherein said composition is an aqueous composition.

* * * * *